United States Patent [19]

Helm

[11] Patent Number: 4,899,051
[45] Date of Patent: Feb. 6, 1990

[54] METHOD AND DEVICE FOR SIMULATING THERMAL EFFECTS AT THE INTERFACE OF A MAGNETIC HEAD AND A RECORDING MEDIUM

[75] Inventor: Michael J. Helm, Schenectady, N.Y.

[73] Assignee: Eastman Kodak Company, Rochester, N.Y.

[21] Appl. No.: 286,191

[22] Filed: Dec. 19, 1988

[51] Int. Cl.$^4$ .................. G01N 3/56; G01N 21/84
[52] U.S. Cl. .................. 250/340; 250/341; 73/7; 73/866.4; 374/130
[58] Field of Search ............ 73/7, 866.4; 374/134, 374/121, 130, 131, 45, 46, 57; 250/338.1, 340

[56] References Cited

U.S. PATENT DOCUMENTS

| | | | |
|---|---|---|---|
| 3,359,783 | 12/1967 | Scheiman et al. | 73/7 |
| 3,612,891 | 10/1971 | Ward et al. | 73/7 X |
| 3,635,085 | 1/1972 | Shimotsuma et al. | |
| 3,681,682 | 8/1972 | Cox et al. | |
| 3,745,816 | 7/1973 | Erickson et al. | 73/866.4 X |
| 3,753,093 | 8/1973 | Gardner et al. | 73/7 X |
| 4,091,654 | 5/1978 | Hurtig et al. | 73/7 |
| 4,599,266 | 7/1986 | Nakayoma et al. | 360/134 X |

Primary Examiner—Tom Noland
Attorney, Agent, or Firm—Dennis P. Monteith

[57] ABSTRACT

A device, for simulating temperature effects at the interface of a head-to-medium interface, is comprised of a unitary block of material which transmits radiation in the infrared (IR) region of the electromagnetic spectrum and which has a wear-resistant property substantially approximating that of the material of an actual magnetic head to be simulated. The unitary block is shaped to have (1) a first forwardly facing surface substantially approximating the dimensions and contour of the working surface of the head to be simulated, and (2) a second rearwardly facing surface substantially approximating the dimensions and contour of a light-transmitting surface of a positive spherical lens the focal plane of which coincides with the forwardly facing surface. Sapphire is selected as a material having a suitable IR-transmitting property and a wear-resistant-property commensurate with one wear-resistant properties of alloy and ferrite materials commonly used in the manufacture of a video magnetic head.

5 Claims, 3 Drawing Sheets

METHOD AND DEVICE FOR SIMULATING THERMAL EFFECTS AT THE INTERFACE OF A MAGNETIC HEAD AND A RECORDING MEDIUM

BACKGROUND OF THE INVENTION

1. Field of the Invention

The invention relates to measuring the susceptibility of a magnetic transducer head to wear. More specifically, the invention relates to a method and device for simulating thermal effects at the interface of a magnetic head and a magnetic recording medium.

2. Background of Related Art

The interface between a magnetic head and a recording medium is a major concern in a recording system. Ideally, the head should make intimate contact with the recording medium to minimize spacing loss. The head and the medium, on the other hand, should move relative to each other free and easy to minimize wear and tear on both.

Aside from its magnetic characteristics, wear rate and dimensional stability are two of the most important factors of a magnetic head. Of these, wear is a prime consideration. To extend its useful life, the design of a magnetic head and its surface material, where it contacts a recording medium, have been the object of much study.

As a part of that study, it is desirable to determine the ability of the magnetic head (record and playback) to withstand wear at its interface with the recording medium, before magnetic recording/playback apparatus is marketed commercially. Knowing the wear-resistant capability of a magnet head is particularly important for high-density magnetic recording apparatus because even the smallest of wear-induced abnormalities at the head-to-medium interface can contribute to degradation of high-resolution (short wavelength) information.

A commonly employed procedure for determining wear-resistant capability of a magnetic head is to transport a magnetic storage medium (either tape or disk) in operative contact with the head for an extended period of time, e.g. several hours or more. For example, U.S. Pat. No. 4,091,654 discloses a device and method for testing the abrasive quality of a magnetic recording head. The recording head is a "dummy" made of polished steel or other material, the smoothness of which has been determined prior to the head actually contacting a magnetic recording surface. After a given amount of contact between the dummy head and a magnetic tape, a fiber optic emitter/detector measures the smoothness of the head by means of converting light reflected from the surface of the head into a corresponding voltage output.

A problem with a procedure of this type is that it provides no information concerning the rate at which the transducer head is wearing during the tape transport interval. Furthermore, the test fails to identify specific sub-microscopic regions of the head where wear actually occurs.

U.S. Pat. No. 3,753,093 discloses a device for determining the degree of abrasiveness of a magnetic tape. To that end, the tape passes over a simulated recording head which is made from an electrically nonconducting material and which geometrically approximates the dimensions of an actual recording head at its interface with the tape. The working surface of the simulated recording head, i.e. the surface that actually contacts the tape, has deposited thereon one or more strips of a magnetic alloy similar to the magnetic alloy of an actual recording head. Each strip extends from one simulated pole tip to the other simulated pole tip (across the length of a simulated head gap) in the direction of tape-transport movement. During a tape-transport operation, electrical test equipment monitors the increase in the electrical resistance of the magnetic alloy strip to determine the abrasiveness of the magnetic tape.

Although a procedure of this type is intended to provide information concerning the rate at which a magnetic alloy strip is wearing, it also suffers from a disadvantage in that sub-microscopic areas of the head subject to wear and are not readily identifiable by the measurements made; furthermore, the procedure requires a complex, and therefore expensive, multi-step process for depositing the strips of magnetic alloy and for depositing conducting gold films that are needed to provide electrical contact between each alloy strip and the electrical test equipment.

Summary Of The Invention

In view of the foregoing, an object of the invention is to provide apparatus of simple design and construction, and economical to manufacture, for simulating in real time the susceptibility of a magnetic transducer head to wear at its interface with a magnetic recording medium.

Thermal effects, particularly of the type known as hot spots, can be detrimental to the performance of a magnetic transducer head. Accordingly, this object is achieved by a simulated magnetic transducer head fabricated to provide a direct measurement of temperatures as they occur at the head-to-medium interface. To that end, the simulated magnetic head is comprised of a unitary block of material which transmits infrared radiation (IR) and which has a wear-resistant property substantially approximating that of an actual magnetic transducer head. The block is shaped to have (1) a first forwardly facing surface geometrically closely approximating the dimensions and contour of the working surface of an actual magnetic head, and (2) a second rearwardly facing surface geometrically closely approximating the dimensions and contour of a light-transmitting surface of a positive spherical lens the focal plane of which coincides with the first forwardly facing surface. With this geometry, when the first working surface interfaces with a magnetic storage medium, the lens-shaped light-transmitting surface of the material collects IR emitted at its focal plane, e.g. the head-to-medium interface, and transmits the IR collected as a beam of collimated light.

In one arrangement for measuring IR, the lens-shaped surface of the device directs collimated IR onto a detector, the intensity distribution of the infrared across the detector being indicative of temperatures generated at the head-to-medium interface. In an alternate arrangement, a focusable lens, disposed between the simulated head and the detector, focuses IR onto the detector to provide a spatial distribution of the temperatures at the head-to-medium interface. In a further arrangement, a diffraction grating, disposed between the simulated magnetic head and the detector, provides a means for separating the IR into its spectral components. Temperatures at the head-to-medium interface are a function of both the wavelength and the intensity of the IR emitted.

By means of monitoring the intensity and/or wavelength of the infrared emitted, a profile of temperatures at the head-to-medium interface can be monitored. The higher temperatures observed would be indicative of potentially deleterious high friction stress points that are most apt to cause head defects and/or abnormalities detrimental to a magnetic recording and/or playback apparatus.

This advantage, as well as other advantages of the invention, such as a simulated magnetic head of unitary construction, will become more apparent in the detailed description of a preferred embodiment presented below.

BRIEF DESCRIPTION OF THE DRAWINGS

The invention will be described with reference to the accompanying drawings, wherein.

DETAILED DESCRIPTION OF A PREFERRED EMBODIMENT

Figure 1:
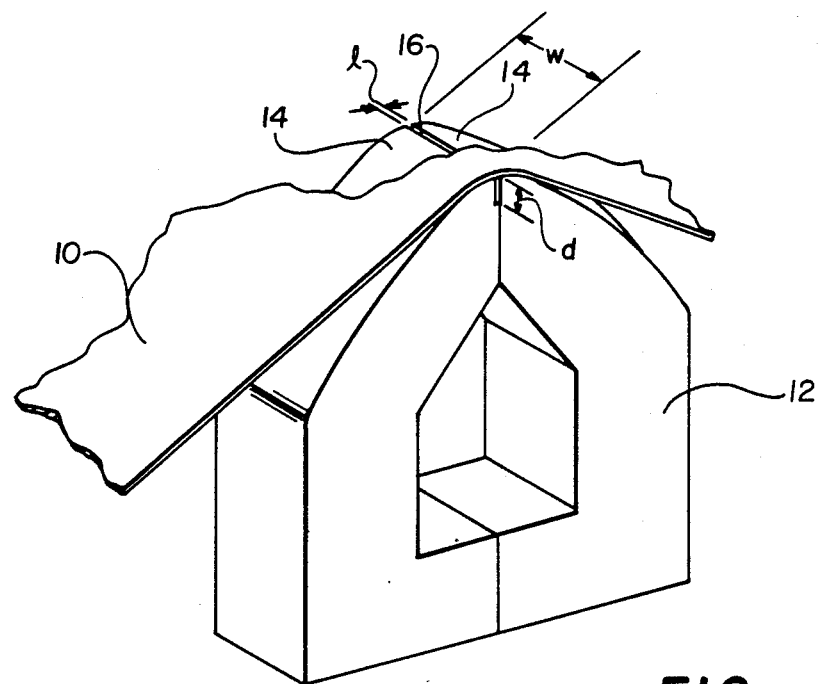
FIG. 1 is a perspective view of a magnetic tape in operative contact with a magnetic head of a design known in the art, with a portion of the tape removed to more clearly illustrate the head-to-tape interface.

FIG. 1 shows a magnetic tape 10 in operative contact with a magnetic head 12 for effecting either the transfer of signal information to the tape (record) or the recovery of signal information from the tape (play back). For either purpose, the tape 10 intimately contacts a contoured working surface 14 of the head 12 on opposing sides of a head gap 16 of length l, depth d, and width w, as relative movement between the head and tape is effected. The head 12 of FIG. 1 is not drawn to scale in order to clearly illustrate pertinent features of a head-to-medium interface.

Figure 2:
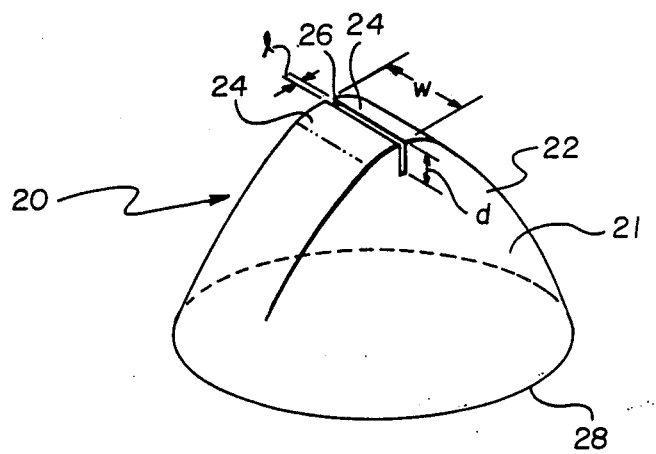
FIG. 2 is a perspective view of a device, constructed in accordance with the invention, for simulating temperature effects at the interface of the magnetic head of FIG. 1 and a magnetic recording medium.

FIG. 2 shows a device 20, constructed in accordance with the teachings of the present invention, for simulating head temperature effects at its interface with a magnetic recording medium. Toward that end, the device 20 is comprised of a unitary block 21 of material 22 having the property of transmitting radiation in the infrared region of the electromagnetic spectrum; furthermore, the material 22 has a wear-resistant property substantially approximating the wear-resistant property of the magnetic head to be simulated. Although various types of magnetic heads are to be simulated, of particular interest is a head, used for high-frequency video recording, of the type made of an alloy (permalloy, alperm, sendust) or of the type made of a ferrite (vacuum-sintered, single-crystal, hot-pressed). To those ends, I have selected sapphire as a material having a suitable IR-transmitting property and a wear-resistant property commensurate with the wear-resistant properties of alloy and ferrite materials commonly used in the manufacture of a video magnetic head.

For the purpose of simulating temperature effects of the magnetic head 12 of FIG. 1, for example, the device 20 has a first forwardly facing surface 24 substantially approximating the dimensions and contour of the aforementioned working surface 14 of the head 12. For those purposes, the surface 24 includes a gap 26, which like the gap 16 of FIG. 1, is of length l, depth d, and width w; furthermore, the surface 24, on opposing sides of the gap 26, has a contour substantially identical to the contour of the working surface 14 of the head 12.

Further toward achieving the object of the invention, the device 20 has a second rearwardly facing surface 28 in the shape of a major surface of a positive spherical lens having a focal plane that coincides with the surface 24. In other words, the surface 28 is fine ground to the shape of a positive spherical lens having a focal point which coincides with the surface 24.

In fabricating the simulated head, the block 21 is ground, contoured, lapped and polished precisely at its forwardly facing surface 24 in order to simulate the physical contact which occurs between the working surface of an actual magnetic head and a recording medium. To that end, a gap of length l less than 0.3 microns ($\mu$) is formed to simulate a state-of-art video head. Similarly, the rearwardly facing surface is precisely ground and polished to form a major lens-shaped surface of appropriate dimensions.

Figure 3:
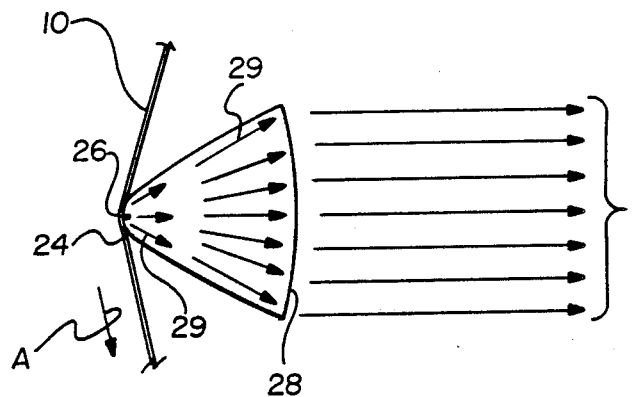
FIG. 3 is a cross-sectional view of the device of FIG. 2 illustrating the principle by which the susceptibility of a magnetic head to wear is measured.

FIG. 3 illustrates the principle by which the device 20 is used to measure the susceptibility of a magnetic head to wear. the tape 10 moves in the direction of the arrow A across the gap 26 in intimate contact with the working surface 24. Frictional action between the surface 24 and the tape 10 generates infrared radiation corresponding to heat produced at their interface. Since the tip of the surface 24 coincides with the focal point of the lens-shaped surface 28 and since the material 22 transmits IR, the surface 28 collects thermal radiation, denoted 29, emitted by friction and transmits the radiation collected outwardly from the device 20 in the form of a beam of collimated light. The temperatures generated are a function of both the intensity and the frequency of the IR.

Figure 4:
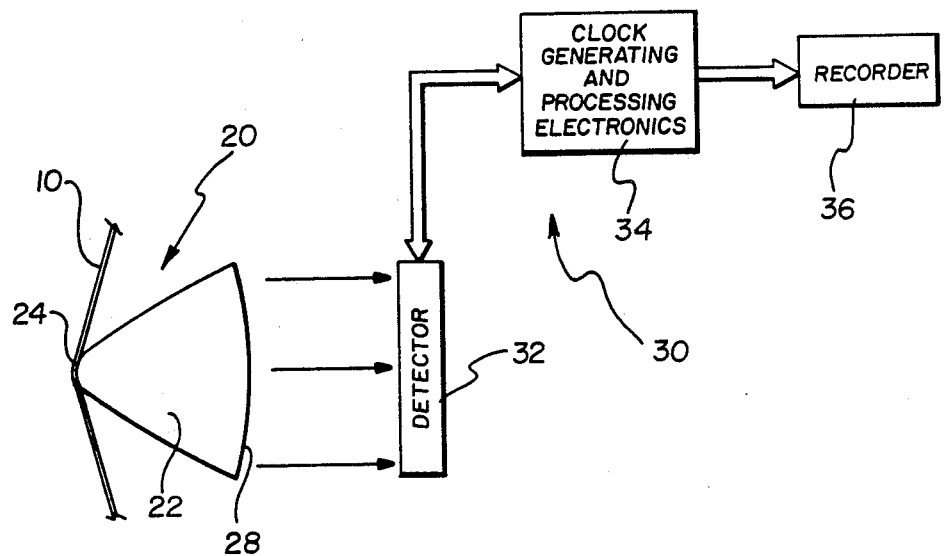
FIGS. 4-6 are schematics of various arrangements using the device of FIG. 2 for measuring thermal effects at the interface of a magnetic head and a magnetic recording medium.

FIG. 4 illustrates apparatus 30 for measuring the intensity of the IR transmitted as a function of time. To that end, a two-dimensional detector 32 is positioned on the optical axis of the device 20. The lens-like surface 28 images IR transmitted from the device 20 onto the detector 32. The detector 32 may be a vidicon or a solid state area detectir e,g, CCD, CID or MOS imager.

For the case of a solid state detector, clock generating electronics 34 function to control the detector 32 and to process its output signals in a known manner. An appropriate recorder 36, coupled to an output of the electronics 34, serves for making a temporal record of the IR transmitted.

Figure 5:
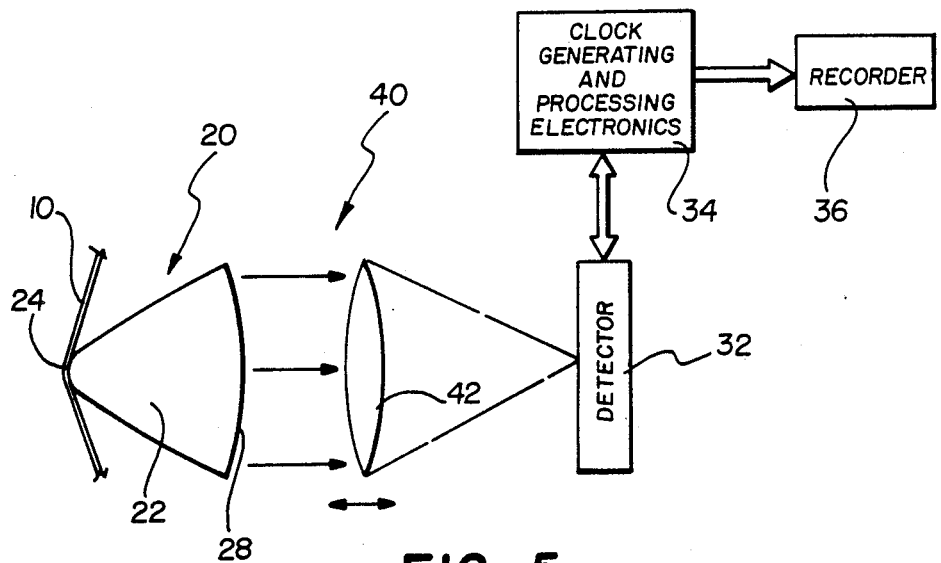

FIG. 5 illustrates apparatus 40 for measuring both the temporal distribution and the spatial distribution of IR produced at the interface of the surface 24 and the tape 10. For those purposes, a focusable lens 42 serves to image the IR onto the detector 32. The aforementioned clock generating electronics 34 and the recorder 36 cooperatively function to make a record of the temporal and spatial distribution of the IR. With this arrangement, hot spots at the head-to-medium can be pinpointed.

The tip surface of the device 20, like the working surface of an actual magnetic head, is buffed away by frictional action of the tape. This buffing action causes the gap 26 to lengthen. Thus, as the tip of the device 20 is reduced by wear, it can be expected that the bandwidth of the radiation, as well as its intensity, will vary with time.

Figure 6:
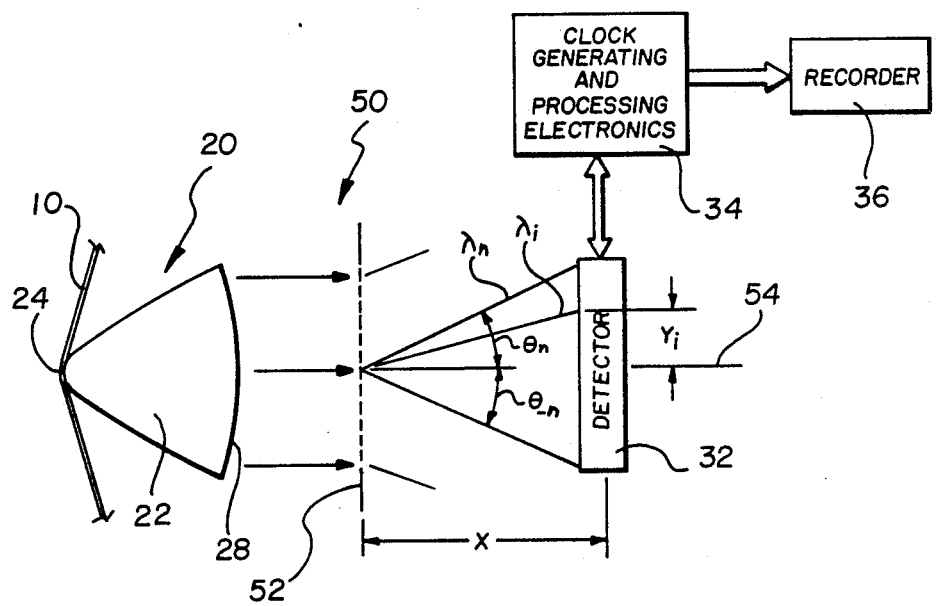

FIG. 6 illustrates apparatus 50 for measuring both the intensity and the frequency of IR produced at the interface of the surface 24 and the tape 10. To that end, a diffraction grating 52, located a given distance, x, from the detector 32, serves to disperse incident radiation according to its wavelength, forming duplicate spectra (rainbows) across opposing halves of the detector (on either side of its central axis 54) with progressively longer wavelengths, $\lambda_i$, being diverted to progressively higher angles $\theta_i$.

Each pixel of the detector 32 receives an amount of radiant energy corresponding to its off-axis position, the repetition frequency of rulings of the diffraction grating 52, and the spectral content of the incident radiation. More specifically, the diffraction grating 52 disperses incident radiant energy across opposite halves of the detector 32 according to:

$$\sin \theta_i = \lambda_i f$$

where f is the repetition frequency of the grating. Note that $$\sin \theta_i = y_i/(y_i^2 + x^2)^{\frac{1}{2}}$$

where $y_i$ is the distance the ith pixel is from the axis 54.

Alternatively, a stationary detector 32 of multiple pixels may be replaced by a movable detector having only a single photosite. With this arrangement, the detector moves preferably in a stepwise manner along a linear path, orthogonal to the axis 54 a given distance x from the diffraction grating 52. The output of the movable detector at each stepwise position corresponds to the radiant energy, incident to the detector, at a particular wavelength.

The invention has been described in detail with particular reference to a presently preferred embodiment, but it will be understood that variations and modifications can be effected within the spirit and scope of the invention.

What is claimed is:

1. A device for simulating wear of a magnetic transducer head at a working surface thereof, i.e. at its interface with a magnetic storage medium, said device comprising a block of material which transmits infrared radiation and which has a wear-resistant property approximating that of the actual magnetic transducer head, said block having (1) a first forwardly facing working surface geometrically substantially approximating the dimensions and contour of the working surface of the magnetic head to be simulated, and (2) a second rearwardly facing surface geometrically substantially approximating the dimensions and contour of a light transmitting surface of a positive spherical lens, to cause said rearwardly facing surface to collect and to direct infrared radiation emitted at an interface between said first working surface and the magnetic storage medium.

2. A device according to claim 1 wherein said material is sapphire.

3. A device according to claim 1 wherein infrared radiation is directed from said rearwardly facing surface onto a detector.

4. A device for simulating wear of a magnetic transducer head a working surface thereof, i.e. at its interface with a magnetic storage medium, said device comprising a unitary block of material which transmits infrared radiation and which has mechanical properties of the magnetic transducer head to be simulated, said block defining (1) a first forwardly facing surface geometrically closely approximating the dimensions and contour of the working surface of the head to be simulated, and (2) a second rearwardly facing surface geometrically closely approximating the dimensions and contour of a light-transmitting surface of a positive spherical lens the focal plane of which coincides with said first working surface, to cause said rearwardly facing surface to collect and to collimate infrared radiation emitted at an interface between said first working surface and the magnetic storage medium in response to relative movement therebetween and to direct the collimated infrared radiation outwardly from said second surface.

5. A method for simulating wear of a magnetic transducer head comprising:
   (a) simulating an actual magnetic transducer head with an infrared transmitting material having a wear-resistant property approximating that of the actual magnetic head and configured to have (1) a working surface geometrically closely approximating the dimensions and contour of a working surface of the actual head, and (2) an opposing surface geometrically closely approximating the dimensions and contour of a light-transmitting surface of a positive spherical lens;
   (b) moving a magnetic storage medium in transducing relationship over the working surface of the infrared transmitting material; and
   (c) transmitting infrared radiation emitted at the interface between said working surface and the magnetic storage medium through the opposing surface of the material onto a detector.

* * * * *